United States Patent
Hamilton

(10) Patent No.: US 6,841,772 B1
(45) Date of Patent: Jan. 11, 2005

(54) EYE-PROTECTION DEVICE HAVING DUAL HIGH VOLTAGE SWITCHING

(75) Inventor: Thomas J. Hamilton, Holland, MI (US)

(73) Assignee: Jackson Products, Inc., St. Charles, MO (US)

( * ) Notice: Subject to any disclaimer, the term of this patent is extended or adjusted under 35 U.S.C. 154(b) by 0 days.

(21) Appl. No.: 10/139,837

(22) Filed: May 3, 2002

Related U.S. Application Data

(60) Provisional application No. 60/288,760, filed on May 5, 2001.

(51) Int. Cl.$^7$ .................................................. H01J 40/14
(52) U.S. Cl. ................... 250/214 B; 349/14; 250/201.1
(58) Field of Search .............................. 250/201.1, 250, 250/214 B; 349/13, 14, 116; 359/220

(56) References Cited

U.S. PATENT DOCUMENTS

| | | |
|---|---|---|
| 2,423,320 A | 7/1947 | Hurley |
| 2,548,230 A | 4/1951 | Molyneux |
| 2,761,048 A | 8/1956 | Herrick et al. |
| 3,137,784 A | 6/1964 | Kasemann |
| 3,159,844 A | 12/1964 | Haboush |
| 3,245,315 A | 4/1966 | Marks et al. |
| 3,575,491 A | 4/1971 | Heilmeier |
| 3,731,986 A | 5/1973 | Fergason |
| 3,873,804 A | 3/1975 | Gordon |
| 3,881,808 A | 5/1975 | Gurtler et al. |
| 3,881,809 A | 5/1975 | Fergason et al. |
| 3,890,628 A | 6/1975 | Gurtler |
| 3,918,796 A | 11/1975 | Fergason |
| 3,967,881 A | 7/1976 | Moriyama et al. |
| 4,039,803 A | 8/1977 | Harsch |
| 4,071,912 A | 2/1978 | Budmiger |
| RE29,684 E | 6/1978 | Gordon |
| 4,155,122 A | 5/1979 | Budmiger |
| 4,237,557 A | 12/1980 | Gordon |
| 4,240,709 A | 12/1980 | Hornell |

(List continued on next page.)

FOREIGN PATENT DOCUMENTS

| | | |
|---|---|---|
| DE | DT 2315308 | 10/1973 |
| EP | 0157744 | 9/1985 |
| EP | 0335056 | 4/1989 |
| EP | 0349665 | 10/1990 |
| FR | 2530-039 A | 1/1984 |
| GB | 325586 | 2/1930 |
| JP | 59-92276 | 7/1980 |
| JP | 59-111102 | 6/1984 |
| SE | SW 73127334 | 7/1977 |
| SE | SW 7608690-9 | 2/1979 |
| WO | WO 90/14809 | 12/1990 |

*Primary Examiner*—Thanh X. Luu
(74) *Attorney, Agent, or Firm*—Dunlap, Codding & Rogers, P.C.

(57) ABSTRACT

An auto darkening eye protection device comprising a shutter assembly and a control circuit. The shutter assembly is adjustable between a clear state and a dark state. The control circuit comprises a sensing circuit, a weld detect circuit, and a delivery circuit. The sensing circuit senses incident light and provides an output indicative of the incident light. The weld detect circuit receives the output of the sensing circuit, and enables a dark state drive signal to be delivered to the shutter assembly. The delivery circuit outputs the dark state drive signal to the shutter assembly to switch the shutter assembly from the clear state to the dark state upon enablement by the weld detect circuit. The dark state drive signal includes a high voltage pulse followed by a stable AC waveform. The high voltage pulse is formed by a positive voltage signal and a negative voltage signal.

22 Claims, 7 Drawing Sheets

U.S. PATENT DOCUMENTS

| | | |
|---|---|---|
| 4,279,474 A | 7/1981 | Belgorod |
| 4,328,490 A | 5/1982 | Usuba et al. |
| 4,385,806 A | 5/1983 | Fergason |
| 4,435,047 A | 3/1984 | Fergason |
| 4,436,376 A | 3/1984 | Fergason |
| 4,540,243 A | 9/1985 | Fergason |
| 4,556,289 A | 12/1985 | Fergason |
| 4,560,239 A | 12/1985 | Katz |
| 4,582,396 A | 4/1986 | Bos et al. |
| 4,664,479 A | 5/1987 | Hiroshi |
| RE32,521 E | 10/1987 | Fergason |
| 4,710,694 A | 12/1987 | Sutphin et al. |
| 4,728,173 A | 3/1988 | Toth |
| 4,759,608 A | 7/1988 | Yang |
| 4,813,766 A | 3/1989 | Keene et al. |
| 4,821,292 A | 4/1989 | Childress |
| 4,863,244 A | 9/1989 | Fuerthbauer et al. |
| 4,877,310 A | 10/1989 | Seachman et al. |
| 4,901,074 A | 2/1990 | Sinn et al. |
| 4,928,181 A | 5/1990 | Harward |
| 5,015,086 A | 5/1991 | Okaue et al. |
| 5,074,647 A | 12/1991 | Fergason et al. |
| 5,113,270 A | 5/1992 | Fergason |
| 5,184,156 A | 2/1993 | Black et al. |
| 5,208,688 A | 5/1993 | Fergason et al. |
| 5,248,880 A | 9/1993 | Fergason |
| 5,252,817 A | 10/1993 | Fergason et al. |
| 5,347,383 A | 9/1994 | Fergason |
| 5,377,032 A | 12/1994 | Fergason et al. |
| 5,420,502 A | 5/1995 | Schweitzer, Jr. |
| 5,519,522 A | 5/1996 | Fergason |
| 5,671,035 A | 9/1997 | Barnes |
| 5,751,258 A | 5/1998 | Fergason et al. |
| 6,067,129 A | 5/2000 | Fergason |
| 6,070,264 A | 6/2000 | Hamilton et al. |
| 6,614,409 B1 * | 9/2003 | Bae .................... 345/8 |

* cited by examiner

EYE-PROTECTION DEVICE HAVING DUAL HIGH VOLTAGE SWITCHING

CROSS-REFERENCE TO RELATED APPLICATIONS

The present application claims priority to the provisional patent application identified by U.S. Ser. No. 60/288,760 and filed on May 5, 2001, the entire content of which is hereby expressly incorporated by reference.

DETAILED DESCRIPTION OF THE INVENTION

Figure 1:
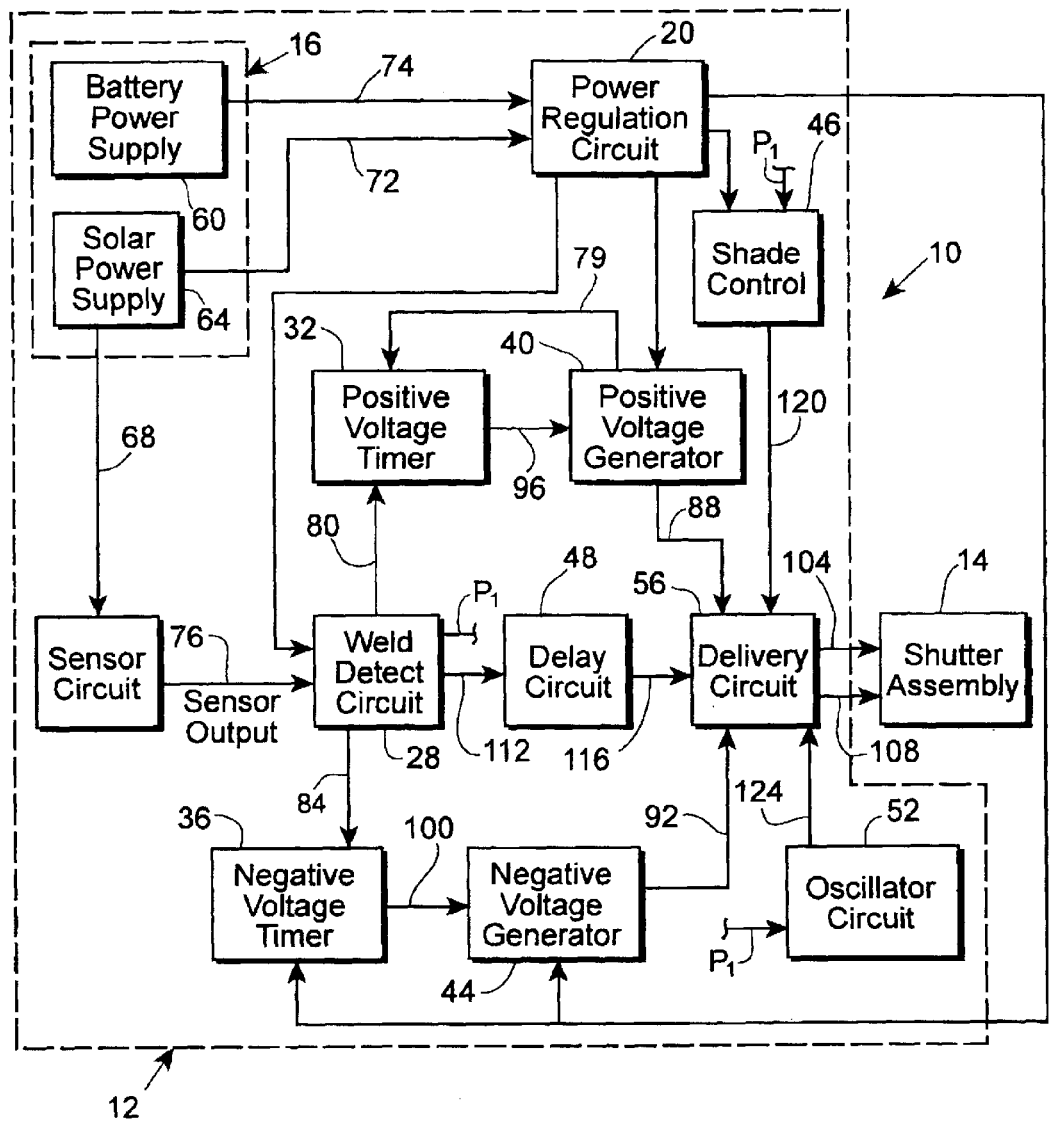
FIG. 1 is a block diagram of an eye protection device constructed in accordance with the present invention.

Referring now to the drawings, and in particular to FIG. 1, shown therein and designated by the reference numeral 10 is an eye protection device constructed in accordance with the present invention. In general, the eye protection device 10 is designed to automatically darken in the presence of an intense light, such as a welding arc. The eye protection device 10 is preferably adapted to be worn by an individual. For example, the eye protection device 10 can be implemented in the form of a cassette 11 (FIGS. 4–8) suitable for mounting in a welding helmet (not shown).

The eye protection device 10 is provided with a control circuit 12, and a shutter assembly 14. The shutter assembly 14 is an auto-darkening filter capable of being driven between a clear state and a dark state. In the clear state, an individual can see through the shutter assembly 14 under ambient light conditions. In the dark state, the shutter assembly 14 becomes opaque so that the individual can only see through the shutter assembly 14 in the presence of an intense light, such as a welding arc.

The switching speed of the eye protection device 10 is an important performance attribute of the eye protection device 10. As will be well understood by those skilled in the art, the switching speed is the time period for switching the shutter assembly 14 from the clear state to the dark state. As will be discussed in more detail below, in accordance with the present invention, a dark state drive signal having a high voltage, e.g. 30 V, is provided to the shutter assembly 14 to enhance the switching speed of the shutter assembly 14. The shutter assembly 14 is preferably a liquid crystal display, such as a twisted nematic liquid crystal display.

The control circuit 12 senses the intense light and outputs the dark state drive signal to the shutter assembly 14 to cause the shutter assembly 14 to switch from the clear state to the dark state. If the control circuit 12 senses that no welding arc is present, the control circuit 12 will cause a "clear state" drive signal to be delivered to the shutter assembly 14.

In general, the control circuit 12 is provided with a power supply 16, a power regulation circuit 20, a sensor circuit 24, a weld detect circuit 28, a positive voltage timer 32, a negative voltage timer 36, a positive voltage generator 40, a negative voltage generator 44, a shade control circuit 46, a delay circuit 48, an oscillator circuit 52, and a delivery circuit 56.

The power supply 16 includes a battery power supply 60, and a solar power supply 64. The solar power supply 64 provides electrical power to the sensor circuit 24 via a power line 68, and electrical power to the power regulation circuit 20 via a power line 72. The battery power supply 60 provides electrical power to the power regulation circuit 20 via a power line 74.

In accordance with one aspect of the present invention, the power regulation circuit 20 allows the solar power supply 64 to power the sensor circuit 24, and regulates any additional power from the solar power supply 64 to be supplied to the remainder of the control circuit 12. This additional power is preferably regulated from above the voltage of the battery power supply 60 so that the power generated by the solar power supply 64 will be used before any power from the battery power supply 60. This reduces the load on the battery power supply 60 and thereby extends the life of the battery power supply 60.

In general, the solar cell voltage that assists the rest of the control circuit 12 (non-sensor) must be limited to a predetermined voltage, such as 6.4V. To do this, in one preferred embodiment shown in FIG. 2, low current Zener diodes (Z1 and Z2) are used. These Zener diodes (Z1 and Z2) need a minimum of 4 uA to 8 uA for their reference voltage to be stable at 1.22V each. For this to happen, first if the eye protection unit 10 is in the clear state, the shade control circuit 46 is off and (if enough light is on the solar power supply 64) the current must come from the solar power supply 64. This is done through R14. If there is not enough light the reference will not affect the shade. The second state is if the eye protection unit 10 is in the dark state. In the dark state the reference must be accurate. Some solar power can be used, but to make sure the Zener diodes Z1 and Z2 have enough current through them, even at low light, additional current is supplied from the shade control circuit 46 through R50. This will insure the Zener diodes have enough current to maintain a stable voltage to the shade control circuit 46 via a line 75 and thus a stable shade.

Figure 9:
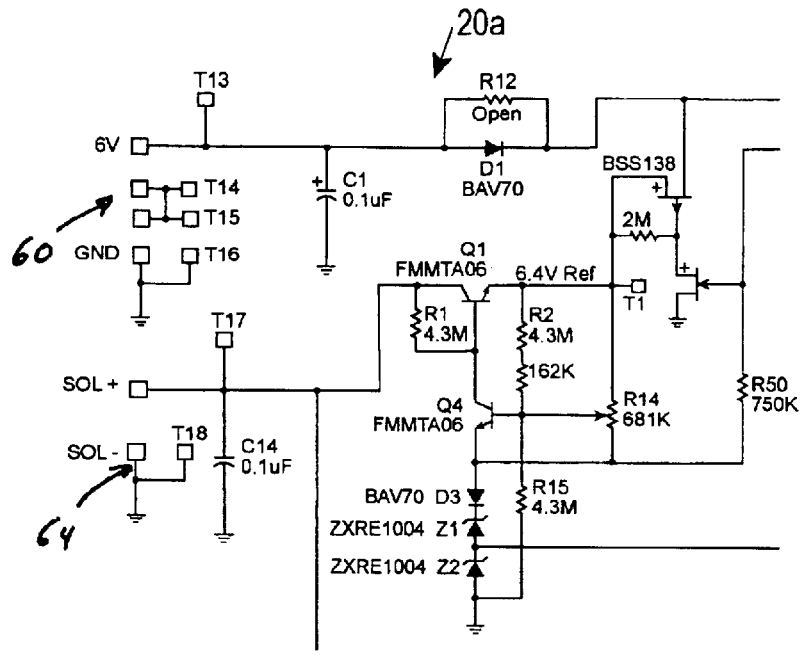
FIG. 9 is a second embodiment of a control circuit constructed in accordance with the present invention for controlling the shutter assembly.
Figure 10:
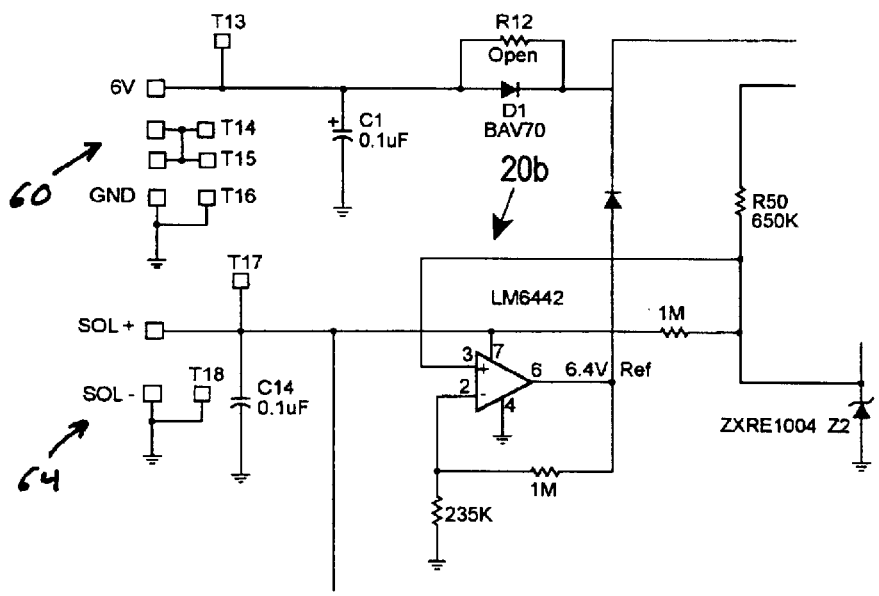
FIG. 10 is a third embodiment of a control circuit constructed in accordance with the present invention for controlling the shutter assembly.

In accordance with the present invention, the regulation of the solar power supply 64 can be implemented in other manners. For example, as shown in FIG. 9, an alternate circuit having a FET is utilized to regulate the solar power supply 64 to maintain the stable reference voltage. As shown in FIG. 10, an op-amp circuit is utilized to regulate the solar power supply 64 to maintain the stable reference voltage.

The battery power supply 60 can be provided with any suitable voltage so as to supply power to the control circuit 12 and the shutter assembly 14. For example, the battery power supply 60 can be provided with a voltage in a range from about 2.0 V to about 6.5 V. In a preferred embodiment depicted in FIG. 2, the battery power supply 60 has about 6 Volts.

The sensor circuit 24 detects the presence of light and outputs a sensor output signal representative of the level of light detected. The sensor output signal is output to the weld detect circuit 28 via a signal path 76. The weld detect circuit 28 enables the drive signal that will be delivered to the shutter assembly 14. In general, if the sensor output signal indicates to the weld detect circuit 28 that an intense light, such as a welding arc is present, the weld detect circuit 28 will cause a dark state drive signal to be delivered to the shutter assembly 14. If the sensor output signal indicates to the weld detect circuit 28 that no welding arc is present, the weld detect circuit 28 will cause a "clear state" drive signal to be delivered to the shutter assembly 14.

The dark state drive signal is provided with two components; a high voltage pulse followed by a stable AC waveform. The high voltage pulse quickly drives the shutter assembly 14 from the clear state to the dark state. The stable AC waveform maintains the shutter assembly 14 in the dark state. The high voltage pulse preferably has a voltage in a range from about 15 V to about 120 V, and a time period from about 10 microseconds to about 100 milliseconds. In general, the voltage of the high voltage pulse will depend on the maximum voltage ratings of the components utilized to implement the control circuit 12. In one preferred embodiment, the voltage of the high voltage pulse is about 30 V, and the time period of the high voltage pulse is about 1 ms.

Figure 3:
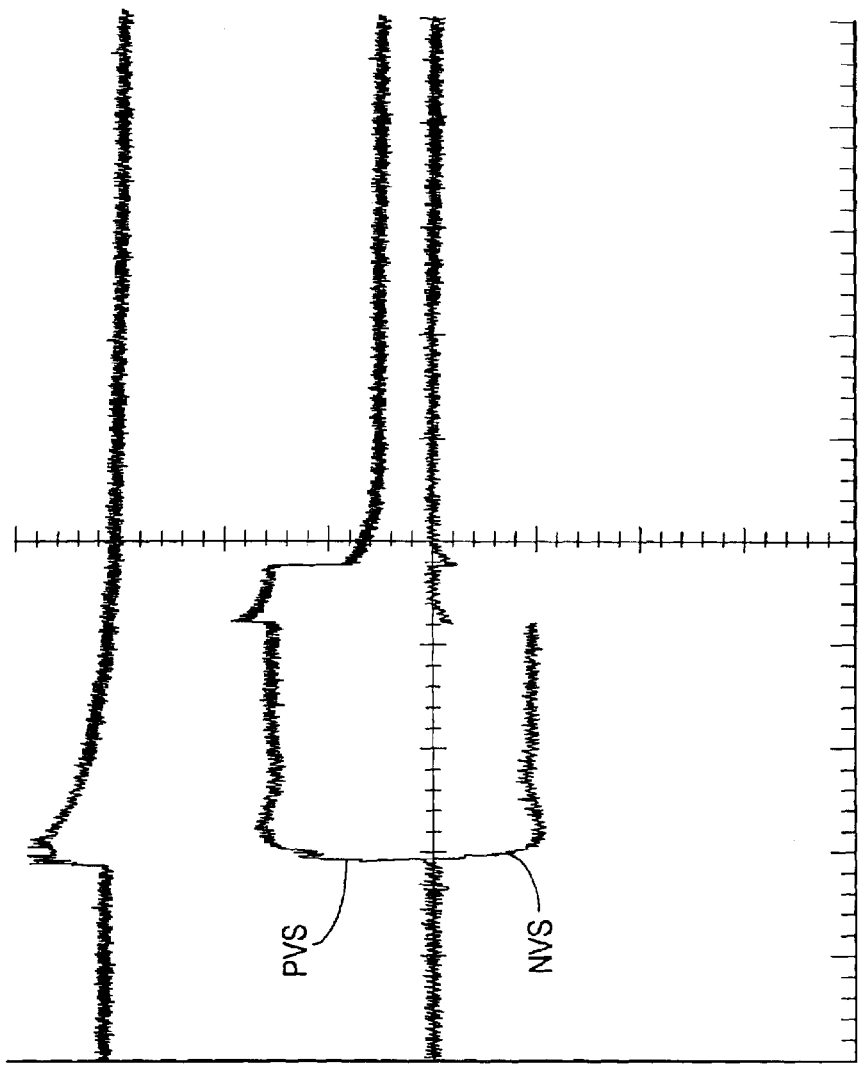
FIG. 3 is a graph illustrating a positive voltage signal and a negative voltage signal in accordance with the present invention.

As shown in FIG. 3, the high voltage pulse is formed by a positive voltage signal (referenced to ground) synchronized with a negative voltage signal (referenced to ground). The positive and negative voltage signals are labeled in FIG. 3 with the designations "PVS" and "NVS". In other words, the leading edges of the positive voltage signal and the negative voltage signals are synchronized. The shutter assembly 14 does not have a ground reference, and therefore, does not differentiate positive or negative. The voltage of the high voltage pulse in the dark state drive signal is thus the difference between the positive voltage signal and the negative voltage signal.

For example, if the positive voltage signal has a magnitude of +18 Volts, and the negative voltage signal has a magnitude of −12 Volts, the voltage of the high voltage pulse would be +18 V−(−12 V)=+30 Volts.

The positive voltage signal is produced by the positive voltage timer 32 and the positive voltage generator 40. The negative voltage signal is produced by the negative voltage timer 36 and the negative voltage generator 44.

The positive voltage timer 32 sets the time period of the positive voltage signal. The positive voltage generator 40 produces the magnitude of the positive voltage signal. Likewise, the negative voltage timer 36 sets the time period of the negative voltage signal. The negative voltage generator 44 produces the magnitude of the negative voltage signal. In one preferred embodiment, the positive voltage generator 40 triples the voltage of the battery power supply 60, and the negative voltage generator 44 doubles the voltage of the battery power supply 60 so that the high voltage pulse has a voltage 5 times the voltage of the battery power supply 60. The positive voltage timer 32 receives electrical power (via a signal path 79) having the increased voltage from the positive voltage generator 40 so that the positive voltage timer 32 can switch components in the positive voltage generator.

The advantage of using the positive voltage signal and the negative voltage signal is that the cost of manufacturing the control circuit 12 is reduced. That is, electrical components which switch over 18 Volts are more expensive than electrical components which switch below 18 Volts. By using the positive voltage signal and the negative voltage signal only one more expensive and higher voltage part, i.e. the delivery circuit 56, is needed to send a voltage higher than 18 Volts to the shutter assembly 14.

When the sensor output signal indicates to the weld detect circuit 28 that an intense light, such as a welding arc is present, the weld detect circuit 28 outputs a signal to the positive voltage timer 32 and the negative voltage timer 36 via signal paths 80 and 84 to cause the positive voltage signal and the negative voltage signal to be fed to the delivery circuit 56 via signal paths 88 and 92. That is, upon receipt of the signal from the weld detect circuit 28, the positive voltage timer 32 and the negative voltage timer 36 output respective timing signals to the positive voltage generator 40 and the negative voltage generator 44 via signal paths 96 and 100. In response thereto, the positive voltage generator 40 and the negative voltage generator 44 output the positive voltage signal and the negative voltage signal to the delivery circuit 56. The delivery circuit 56 outputs the positive voltage signal to the shutter assembly 14 on a signal path 104, and the negative voltage signal to the shutter assembly 14 on a signal path 108 to cause the shutter assembly 14 to switch from the clear state to the dark state.

Then, the weld detect circuit 28 outputs a signal to the delivery circuit 56 via the delay circuit 48 and signal paths 112 and 116 to cause the delivery circuit 56 to enable the stable AC waveform to the shutter assembly 14. The stable AC waveform maintains the shutter assembly 14 in the dark state. The stable AC waveform maintains the shutter assembly 14 in the dark state. The stable AC waveform is preferably a squarewave having a user adjustable magnitude varying from a maximum of about +3.2 V–+4 V to a minimum of about −3.2V−−4 V. The stable AC waveform can be provided with other shapes, such as a sinusoidal shape, however, the efficiency of the circuit 12 will be reduced.

The stable AC waveform is produced as follows. The shade control circuit 46 provides a stable DC voltage signal having a magnitude sufficient to maintain the shutter assembly 14 in the dark state to the delivery circuit 56 via a signal path 120. The oscillator circuit 52 provides an oscillating signal to the delivery circuit 56 via a signal path 124 to cause the delivery circuit 56 to produce the stable AC waveform. In one preferred embodiment, the oscillating signal causes the delivery circuit 56 to periodically switch the polarity of the signal transmitted to the shutter assembly 14.

If the sensor output signal indicates to the weld detect circuit 28 that no welding arc is present, the weld detect circuit 28 will cause a "clear state" drive signal to be delivered to the shutter assembly 14 via the delay circuit 48, the delivery circuit 56 and the signal paths 112, 116, 104 and 108. The delay circuit 48 delays the submission of the clear state drive signal to the delivery circuit 56 for a predetermined time, thus preventing the shutter assembly 14 from switching to a clear state during brief "off" periods in the weld pulsations that exist with various weld types. Further, once the welding arc is extinguished, the work piece which is being welded may glow brightly for several milliseconds thereafter. The delay circuit 48 delays the clear state drive signal for desirably between about 0.1 seconds to about 1 seconds, and more desirably between about 0.2 seconds to about 0.4 seconds so as to protect the individual's eyes from the glow from the work piece. The delay circuit 48 may have a fixed time delay, or may be adjustable by a user so as to be set based on the user's preference.

In one preferred embodiment, the weld detect circuit 28 switches power to the oscillator circuit 52 and the shade control circuit 46 via a signal path P1 to conserve battery power. That is, in the preferred embodiment, the oscillator circuit 52 and the weld detect circuit 28 are only enabled when the weld detect circuit 28 senses the welding arc.

Figure 2A:
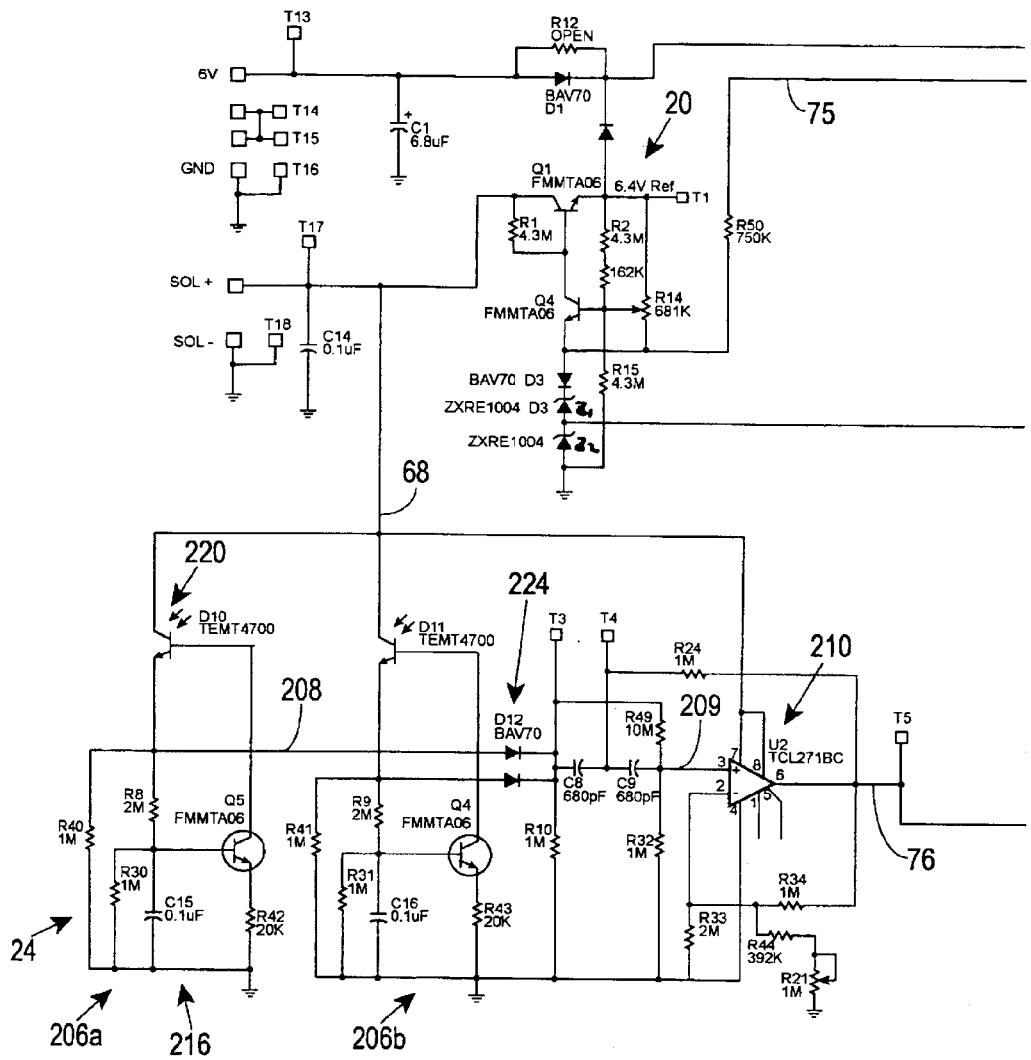
FIGS. 2A–2C cooperatively illustrate a schematic diagram of a control circuit constructed in accordance with the present invention for controlling a shutter assembly.
Figure 2B:
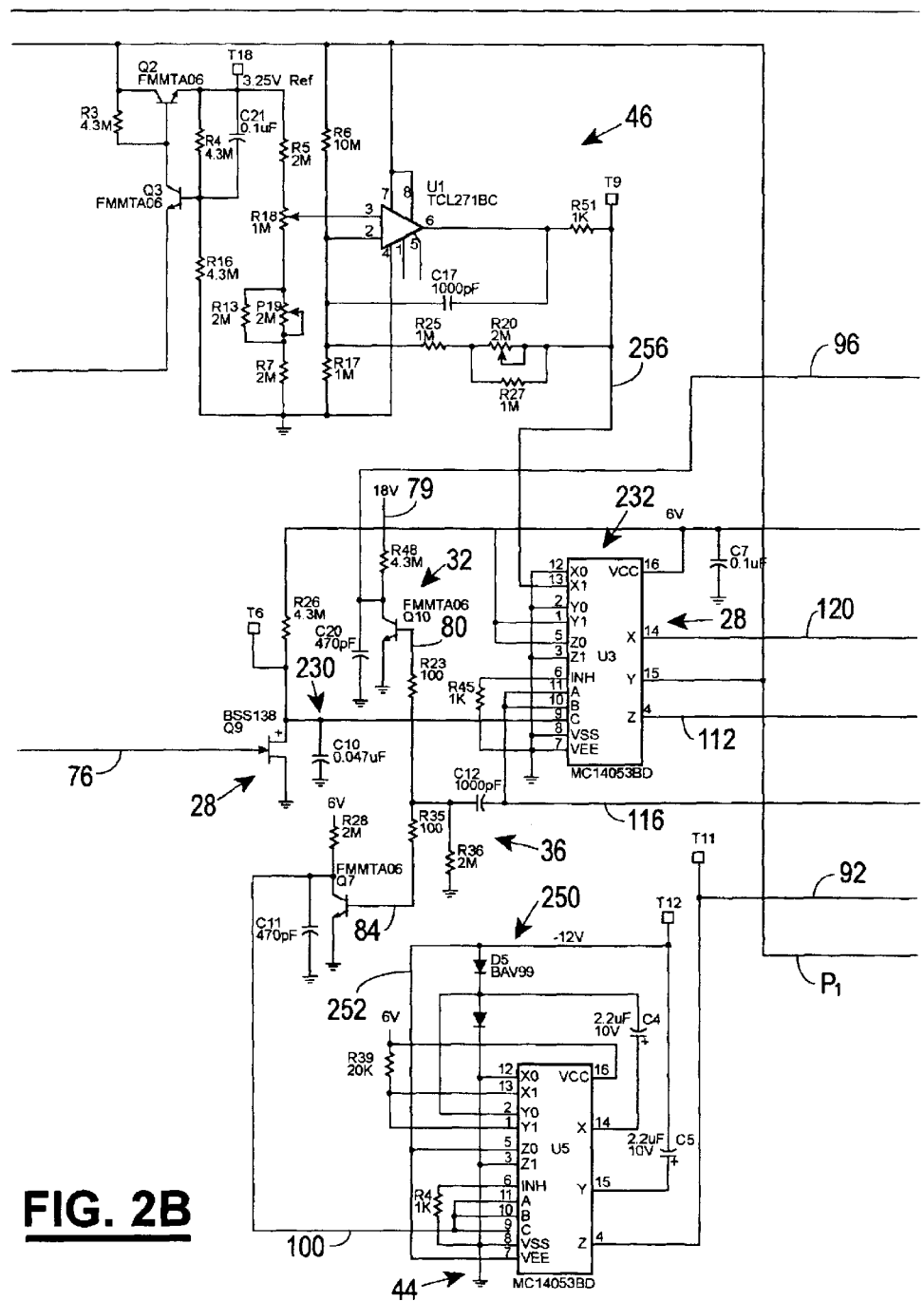
Figure 2C:
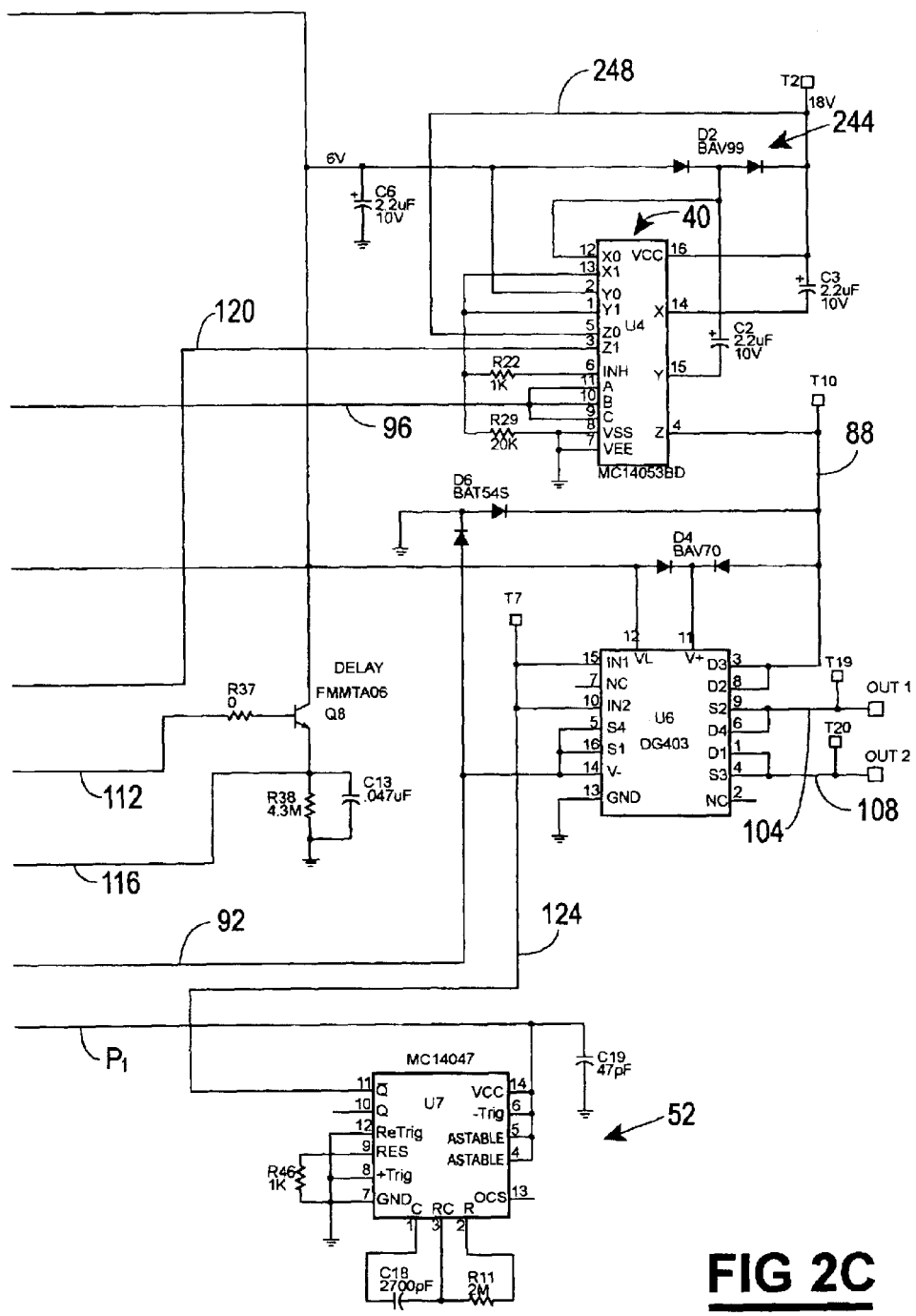

Shown in FIG. 2 is a schematic diagram of one preferred implementation of the control circuit 12.

Figure 4:
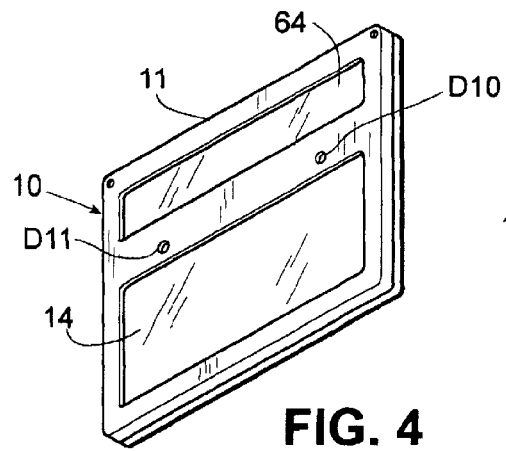
FIG. 4 is a front perspective view of the eye protection device.

Referring now to FIG. 4, shown therein is a front perspective view of the eye protection device 10. The sensor circuit 24 of the eye protection device 10 includes a pair of spatially disposed light detectors, such as phototransistors D10 and D11, for sensing the welding arc.

Figure 5:
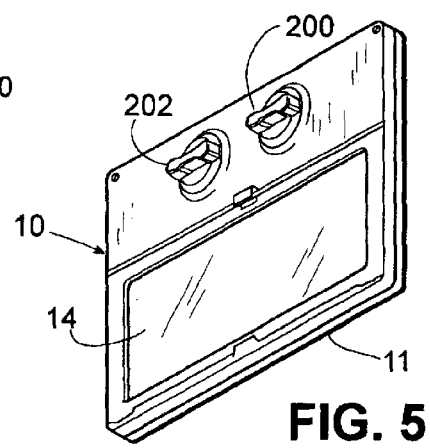
FIG. 5 is a rear perspective view of the eye protection device.
Figure 6:
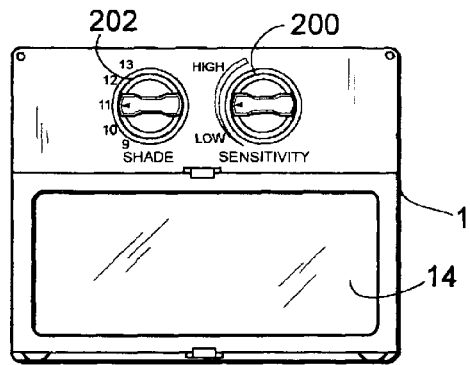
FIG. 6 is a rear elevational view of the eye protection device.
Figure 8:
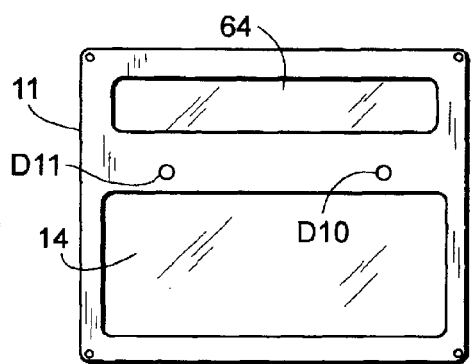
FIG. 8 is a front elevational view of the eye protection device.
Figure 7:
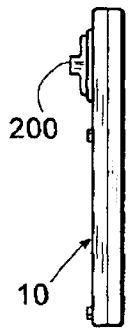
FIG. 7 is a side elevational view of the eye protection device.

The eye protection device 10 can be provided with a plurality of controls for controlling various settings thereof. For example, as shown in FIG. 5, the eye protection device 10 can be provided with a first knob 200 and a second knob 202 for adjusting the sensitivity and the shade of the eye protection device 10. The first and second knobs 200 and 202 can be connected to any suitable component for adjusting the settings of the eye protection device 10. For example, the first and second knobs 200 and 202 can be connected to potentiometers.

FIG. 5 is a rear perspective view of the eye protection device.

Referring now to FIG. 2, one embodiment of the control circuit will be described. The sensor circuit 24 includes one or more phototransistor D10 and D11 with the output of each phototransistor D10 and D11 coupled to feedback circuits 206a and 206b. The construction and function of the phototransistors D10 and D11 are similar. Likewise, the feedback circuits 206a and 206b are similar. Thus, only the phototransistor D10 and the feedback circuit 206a will be discussed hereinafter for purposes of brevity.

The output of phototransistor D10 is sent to line 208. A load resistor R40 is connected between line 208 and ground. Additionally, a capacitor C8 couples line 208 to line 209. Resistor R10 is connected between line 208 and ground. Line 209 is also connected to the noninverting input of amplifier 210. Amplifier 210 is preferably configured as closed loop noninverting amplifier wherein the resistors R34, R33, R44 and R21 form an adjustable feedback loop connected to the inverting input of amplifier 210 as shown. In particular, R21 is adjustable to permit the sensitivity of the sensor circuit 24 to be adjusted. The output of amplifier 210 on line 76 serves as the sensor circuit output. Line 76 is connected to the input of the weld detect circuit 28.

The solar power supply 64 powers the phototransistor D10 and amplifier 210 via line 68. Thus, if the solar power supply 64 is left unexposed to incident light, phototransistor D10 and amplifier 210 will not receive power, thus preventing the phototransistor D10 and amplifier 210 from draining the battery power supply 60 when the welding helmet is not in use (when not in use, the welding helmet is typically not exposed to intense light).

The feedback circuit 206a for the phototransistor D10 comprises a resistor capacitor circuit 216 connected between the emitter of the phototransistor and ground, and a feedback transistor Q5 having a base coupled to line 218 of the resistor capacitor circuit 216, a collector coupled to the base of the phototransistor D10, and an emitter coupled to the ground via resistor R42.

Phototransistor D10 serves as the weld sensor. It receives an input of incident light 220 and produces an output on line 208 representative of the intensity of the incident light. The phototransistor D10 used in the present invention is preferably a planar phototransistor configured for a surface mount. The planar phototransistor is smaller than conventional metal can phototransistors, thus allowing a reduction in size of the unit in which the sensor circuit is implemented. While the metal can phototransistors used in the sensor circuits of the prior art had a thickness of about ½ inch, the planar phototransistors with a surface mount used in the present invention have a thickness of only about ¼ inch. This reduction is thickness allows the sensor circuit to be implemented into a smaller and sleeker unit. Further, the surface mount configuration of the phototransistor D10 allows the phototransistor to be easily affixed to a circuit board. The inventor herein has found that the TEMT4700 silicon npn phototransistor manufactured by Vishay-Telefunken is an excellent phototransistor for the present invention as it has a smaller size than conventional metal can phototransistors and allows the sensor circuit to maintain a constant signal level without excessive loading or the drawing of excessive current.

The resistor capacitor circuit 216 and the feedback transistor Q5 in the phototransistor feedback circuit 206a function to adjust the sensitivity of the phototransistor D10. The resistors R30 and R8 and capacitor C15 are chosen to be of a size to provide a relatively large time constant, and therefore a relatively slow response to changes in voltage on line 208. The delay exists because of the time it takes for the voltage on line 218 to charge to an amount sufficiently large to activate Q5. Exemplary values for R30 and R8 are 1 MΩ and 2 MΩ respectively. An exemplary value for C15 is 0.1 $\mu$F. A detailed description of the operation of the resistor capacitor circuit 216 and feedback transistor Q5 can be found in prior patents 5,248,880 and 5,252,817, the disclosures of which have been incorporated by reference.

The signal on line 208 if fed into the amplifier 210. The signal is first passed through a high pass circuit formed by capacitors C8 and C9 to block the DC component of the detected signal. Line 209 contains the DC blocked detected signal. The current on line 209 is diverted to ground via resistor R10.

The sensor circuit 24 operates in the presence of both AC welds and DC welds. In an AC weld (also known as a MIG weld), the welding light is pulsating. Thus, the phototransistor D10 will detect a pulsating light signal. The frequency of the pulsations is often 120 Hz. In a DC weld (also known as a TIG weld), the welding light is substantially continuous, with the exception of a small AC component. When an AC weld is present, the phototransistor will produce a pulsating output on line 208. The variations in the voltage signal due to the pulses will be passed through the capacitors C8 and C9 to line 209 and fed into the amplifier 210. The amplifier 210 will then provide gain for the signal on line 209 which is sufficient to trigger the delivery of the "dark state" drive signal to the shutter assembly 14.

When a DC weld is present, the phototransistor D10 will quickly produce an output on line 208 catching the rising edge of the DC weld. This sudden rise in voltage on line 208 will be passed through to the amplifier 210 causing a signal on line 76 sufficient to trigger the delivery of a "dark state" drive signal to the shutter assembly 400. Thereafter, capacitors C8 and C9 will block the DC component of the DC weld, allowing only the AC variations in the DC weld to pass through to the amplifier 210. A non-reactive element, e.g., resistor R49, is positioned in parallel with the high-pass filter circuit formed by the capacitors C8 and C9. The non-reactive element provides a DC bias to the input of the amplifier 210 to aid in the detection of the DC weld. That is, the brighter the light being generated from the weld becomes, the more sensitive the sensor circuit 24 becomes. In one embodiment, R49 can have a value of 10 M ohm.

The amplifier 210 can be a closed loop, noninverting amplifier as described above. The amplifier 210 can be provided with a feed-back loop formed by R34, R33, R44 and R21. R21 is preferably an adjustable resistor so that the gain of the amplifier 210 and thus the sensitivity of the sensor circuit 24, can be adjusted by the user. Suitable values for R34, R33, R44 and R21 have been found to be 1 M ohm, 2 M ohm, 392 k ohm and 1 M ohm.

The sensor circuit 24 is also provided with an OR logical circuit 224 receiving the outputs from the circuits 206a and 206b. The OR logical circuit 224 permits the highest voltage level from the circuits 206a and 206b to be passed.

The output of the amplifier 210 is fed into the weld detect circuit 28. The weld detect circuit 28 is provided with an electronic switch, an example of which is shown in FIG. 2 as the FET Q9, a delay circuit 230 and a switching circuit 232.

The delay circuit 230 can be formed of a RC circuit and serves to prevent inadvertent switching of the shutter assembly 14 from the dark state to the clear state. That is, the light received by the sensor circuit 24 from the welding arc can be a pulsating signal caused by sputtering of the weld. When the amplifier 210 receives a signal of sufficient magnitude, the output of the amplifier 210 goes high. The high signal is fed to the gate of the FET Q9. FET Q9 then turns on and thereby shorts a capacitor C10 to ground. Once the intensity of the light detected by the sensor circuit 24 decreases, capacitor C10 will begin charging through R26 until the next pulse of intense light is provided to the sensor circuit 24. Thus, the time period of the RC circuit formed by the capacitor C10 and a resistor R26 is selected to maintain the capacitor C10 in a "low" state between pulses to maintain a stable low signal to the switching circuit 232.

The "low" signal is provided to a switch input "C" of the switching circuit 232. This causes the switching circuit 232 to switch between the Z1 and the Z0 inputs. A high signal is applied to the Z0 input and the ground reference is applied to the Z1 input. Thus, when the low signal is provided to the switch input "C", a high signal is provided to the delay circuit 48 via the signal path 112. The delay circuit 48 is provided with an electronic switch as represented by transistor Q8, and an RC circuit as represented by R38 and C13. The high signal switches on the transistor Q8 causing the capacitor C13 to charge. The delay circuit 48 provides a time delay when the control circuit 12 switches from the dark state to the clear state. That is, when the welding stops the workpiece is still glowing brightly. Thus, the time delay of the delay circuit 48 is selected such that the users eyes will be protected until the glow of the workpiece is diminished. The time delay of the delay circuit 48 can vary widely based on user preference. However, suitable time periods range from about 0.2 seconds to about 0.4 seconds. Suitable values for the resistor R38 and the capacitor C13 are 4.3 M ohm and 0.047 micro farads.

The positive voltage timer 32 is formed by resistors R23, R48, transistor Q10 and capacitor C20. The negative voltage timer 36 is formed by resistors R28, R35, transistor Q7 and capacitor C11. The positive and negative voltage timers 32 and 36 serve to properly bias the inputs of the positive and negative voltage generators 40 and 44 to generate the high voltage pulse.

The emitter of the transistor Q8 is connected to the capacitor C12 via the line 116. The capacitor C12 is connected to the base of transistors Q7 and Q10. The transistors Q7 and Q10 short the capacitors C11 and C20, which then have to recharge causing the time frame in which the positive and negative voltage generators 40 and 44 produce the high voltage pulse. This also causes low signals to be provided to switching circuits U4 and U5 via lines 96 and 100.

The positive voltage generator 40 is also provided with at least two capacitors C2 and C3, and a directional control circuit 244. The switching circuit U4 has a plurality of switches X, Y and Z for switching the positive voltage generator between a charging state and a discharging state. Each of the capacitors C2 and C3 are connected to the switching circuit U4 and a reference voltage to establish charging of the capacitors C2 and C3 in the charging state of the switching circuit U4.

Upon receiving the low signal from the positive voltage timer 32, the all of the switches of the switching circuit U4 switch to the discharging state. In the discharging state, the capacitors C2 and C3 are stacked to sum the voltage accumulated on the capacitors. That is, a positive lead of the capacitor C2 is connected to a negative lead of the capacitor C3 through the switch X. Assuming that the voltage reference is 6 V, this would cause a 12 V potential to exist across the stacked capacitors C2 and C3. Further, the negative lead of the capacitor C2 is connected to the reference voltage, e.g., 6 V, through the switch Y so that the positive voltage signal, e.g., +18 V, exists from the ground reference to the positive lead of the capacitor C3. The directional control circuit 244 permits the flow of current between the negative leads of the capacitors C2 and C3 and the reference voltage in the charging state of the switching circuit U4, and prevents the flow of current between the negative leads of the capacitors C2 and C3 in the discharging state of the switching circuit U4 so that the positive voltage signal is generated. The positive voltage signal is then provided to the delivery circuit 56 via lines 248 and 88 through the switch Z.

As shown in FIG. 2, in one embodiment the directional control circuit 244 includes at least two diodes, as designated by the reference numeral D2. Although the directional control circuit 244 has been shown and described as the diodes D2, it should be understood that the directional control circuit 244 could be implemented in other manners. For example, the directional control circuit 244 can be implemented as any device having a P-N junction, such as a transistor, or an enhanced MOSFET.

The value of capacitors C2 and C3 can vary widely depending on the 1) output voltage, 2) load, and 3) length of time for the voltage to switch the shutter assembly 14. For example, in one embodiment the capacitors C2 and C3 can be 2.2 micro farad capacitors. The switching circuit U4 is preferably 1) an integrated circuit having a plurality of electronically controlled switches, or 2) separate electronically controlled switches.

The negative voltage generator 44 is constructed in a similar manner as the positive voltage generator 40, except as discussed hereinafter. The negative voltage generator 44 is provided with a directional control circuit 250 permitting the flow of current between the negative leads of the capacitors C4 and C5 and the reference voltage in the charging state of the switching circuit U5, and preventing the flow of current between the negative leads of the capacitors and the reference voltage in the discharging state of the switching circuit U5. Further, to generate the negative voltage signal, the positive lead of the capacitor C4 is connected to ground in the discharging state of the switching circuit such that the negative voltage signal is produced between the ground reference and the negative lead of the capacitor C5. The negative voltage signal is output to the delivery circuit 56 through switch Z of switching circuit U5 via lines 252 and 92.

When the capacitors C20 and C11 have recharged, a high signal is output to the positive and negative voltage generators 40 and 44 via the lines 96 and 100. The high signal switches the switching circuits U4 and U5 from the discharging state to the charging state to turn off the positive and negative voltage signals.

Once the positive and negative voltage signals have been turned off, a voltage signal is transmitted to the delivery circuit 56 from the shade control 46 through switch X of switching circuit U3 and via lines 256, 120 and 88 to provide the stable AC waveform as discussed above.

As discussed above, in one preferred embodiment, the weld detect circuit 28 switches power to the oscillator circuit 52 and the shade control circuit 46 via a signal path P1 to conserve battery power. That is, in the preferred embodiment, the oscillator circuit 52 and the shade control circuit 46 are only enabled when the weld detect circuit 28 senses the welding arc. To enable the oscillator circuit 52 and the shade control circuit 46, the "B" input of the switching circuit 232 of the weld detect circuit 28 receives a signal on the line 116 when the high signal from the Z output of the switching circuit 232 switches on the transistor Q8 causing the capacitor C13 to charge.

When the sensor circuit 24 no longer senses the welding arc, the signal on the line 116 switches to a "low" state thereby turning off the transistor Q8. This permits the capacitor C13 to discharge through the resistor R38 causing a low state signal to be delivered on the line 116 after a predetermined time period. The low state signal is received by the "A" and "B" inputs of the switching circuit 232 and thereby causes a "low" state signal to be output by the "X" and "Y" outputs. This causes the shutter assembly 14 to switch from the dark state to the clear state and also disables power to the shade control circuit 46 and the oscillator circuit 52 to conserve battery power.

As discussed above, in accordance with one aspect of the present invention, the power regulation circuit 20 allows the solar power supply 64 to power the sensor circuit 24, and regulates any additional power from the solar power supply 64 to be supplied to the remainder of the control circuit 12. This additional power is preferably regulated from above the voltage of the battery power supply 60 so that the power generated by the solar power supply 64 will be used before any power from the battery power supply 60. This reduces the load on the battery power supply 60 and thereby extends the life of the battery power supply 60.

One skilled in the art will recognize that the present invention is susceptible to numerous modifications and variations. For example, the shutter assembly 14 and the control circuit 12 can be implemented in a cassette connectable to a welding helmet, or integrated into the welding helmet. Further, the user controls can be on the cassette or separate from the cassette. For example, the user controls can be implemented as a "pig-tail."

The embodiments of the invention discussed herein are intended to be illustrative and not limiting. Other embodiments of the invention will be obvious to those skilled in the art in view of the above disclosure.

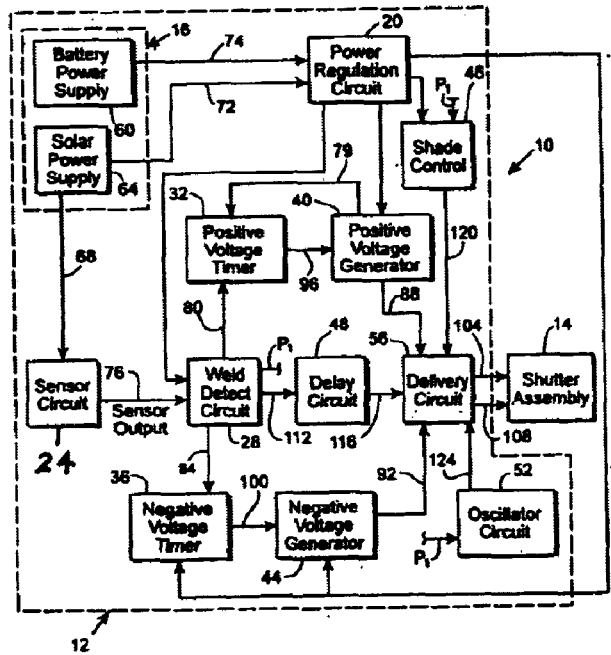

What is claimed is:

1. An auto darkening eye protection device comprising:
   a shutter assembly adjustable between a clear state and a dark state; and
   a control circuit comprising:
      a battery power supply having a voltage;
      a sensing circuit sensing an occurrence of a welding arc and providing an output indicative of the occurrence of the welding arc;
      a weld detect circuit receiving the output of the sensing circuit, the weld detect circuit enabling a dark state drive signal to be delivered to the shutter assembly; and
      a delivery circuit receiving power from the battery power supply and outputting the dark state drive signal to the shutter assembly to switch the shutter assembly from the clear state to the dark state upon enablement by the weld detect circuit, the dark state drive signal including a high voltage pulse followed by a stable AC waveform, the high voltage pulse being formed by a positive voltage signal and a negative voltage signal, the positive voltage signal having a magnitude greater than the voltage of the battery power supply.

2. The auto darkening eye protection device of claim 1 wherein the positive voltage signal and the negative voltage signal are each referenced to ground.

3. The auto darkening eye protection device of claim 1 wherein the high voltage pulse has a voltage in a range from about 15 V to about 120 V, and a time period from about 10 microseconds to about 100 milliseconds.

4. The auto darkening eye protection device of claim 1, wherein the positive and negative voltage signals having leading edges, and wherein the leading edges of the positive and negative voltage signals are synchronized.

5. The auto darkening eye protection device of claim 1, further comprising:
   a positive voltage generator generating the positive voltage signal; and
   a negative voltage generator generating the negative voltage signal, the positive voltage signal and the negative voltage signal being provided to the delivery circuit to form the high voltage pulse.

6. The auto darkening eye protection device of claim 5, wherein the positive voltage generator includes:
   a switching circuit having a charging state and a discharging state;
   at least two capacitors, each of the capacitors connected to the switching circuit and a reference voltage to establish charging of the capacitors in the charging state of the switching circuit, and a positive lead of one capacitor electrically connected to a negative lead of another one of the capacitors in the discharging state of the switching circuit;
   a directional control circuit connected to the capacitors to permit the flow of current between the positive leads of the capacitors and the reference voltage in the charging state of the switching circuit, and to prevent the flow of current between the positive leads of the capacitors and the reference voltage in the discharging state of the switching circuit.

7. The auto darkening eye protection device of claim 6, wherein the directional control circuit includes at least two diodes.

8. The auto darkening eye protection device of claim 5, wherein the negative voltage generator includes:
   a switching circuit having a charging state and a discharging state;
   at least two capacitors, the capacitors connected to the switching circuit and a reference voltage to establish charging of the capacitors in the charging state of the switching circuit, and a positive lead of one capacitor electrically connected to a negative lead of another one of the capacitors in the discharging state of the switching circuit;

a directional control circuit connected to the capacitors to permit the flow of current between the negative leads of the capacitors and the reference voltage in the charging state of the switching circuit, and to prevent the flow of current between the negative leads of the capacitors and the reference voltage in the discharging state of the switching circuit.

9. The auto darkening eye protection device of claim 6, wherein the directional control circuit includes at least two diodes.

10. An auto darkening eye protection device comprising:
a shutter assembly adjustable between a clear state and a dark state; and
a control circuit comprising:
a sensing circuit sensing an occurrence of a welding arc and providing an output indicative of the occurrence of the welding arc, the sensor circuit comprising;
a light sensor having a light sensor output;
an amplifier having an input coupled to the light sensor for amplifying the light sensor output to form the output of the sensing circuit, the output of the sensing circuit sufficient to trigger the weld detect circuit to enable the dark state drive signal when the light sensor receives a light input having an intensity indicative of a welding arc being present;
a high-pass filter circuit positioned between the light sensor and the amplifier for blocking DC voltage and passing high frequency signals; and
a non-reactive element positioned in parallel with the high-pass filter circuit for providing a DC bias to the input of the amplifier representative of the light sensor output;
a weld detect circuit receiving the output of the sensing circuit, the weld detect circuit enabling a dark state drive signal to be delivered to the shutter assembly; and
a delivery circuit outputting the dark state drive signal to the shutter assembly to switch the shutter assembly from the clear state to the dark state upon enablement by the weld detect circuit.

11. The auto darkening eye protection device of claim 10 wherein the amplifier comprises a closed loop non-inverting amplifier.

12. The auto darkening eye protection device of claim 10 wherein the high-pass filter circuit includes a capacitor in circuit between the light sensor and the amplifier.

13. The auto darkening eye protection device of claim 10 wherein the non-reactive element is a resistor.

14. An auto darkening eye protection device comprising:
a shutter assembly adjustable between a clear state and a dark state; and
a control circuit comprising:
a sensing circuit sensing an occurrence of a welding arc and providing an output indicative of the occurrence of the welding arc;
a weld detect circuit receiving the output of the sensing circuit, the weld detect circuit enabling a dark state drive signal to be delivered to the shutter assembly; and
a delivery circuit outputting the dark state drive signal to the shutter assembly to switch the shutter assembly from the clear state to the dark state upon enablement by the weld detect circuit, the dark state drive signal including a high voltage pulse followed by a stable AC waveform, the high voltage pulse being formed by a positive voltage signal and a negative voltage signal, the positive voltage signal being generated for a predetermined period of time.

15. The auto darkening eye protection device of claim 14, wherein the positive voltage signal and the negative voltage signal are each referenced to ground.

16. The auto darkening eye protection device 14 wherein the high voltage pulse has a voltage in a range from about 15 V to about 120 V, and a time period from about 10 microseconds to about 100 milliseconds.

17. The auto darkening eye protection device of claim 14 wherein the positive and negative voltage signals having leading edges, and wherein the leading edges of the positive and negative voltage signals are synchronized.

18. The auto darkening eye protection device of claim 14 further comprising:
a positive voltage generator generating the positive voltage signal; and
a negative voltage generator generating the negative voltage signal, the positive voltage signal and the negative voltage signal being provided to the delivery circuit to form the high voltage pulse.

19. The auto darkening eye protection device of claim 18, wherein the positive voltage generator includes:
a switching circuit having a charging state and a discharging state;
at least two capacitors, each of the capacitors connected to the switching circuit and a reference voltage to establish charging of the capacitors in the charging state of the switching circuit, and a positive lead of one capacitor electrically connected to a negative lead of another one of the capacitors in the discharging state of the switching circuit;
a directional control circuit connected to the capacitors to permit the flow of current between the positive leads of the capacitors and the reference voltage in the charging state of the switching circuit, and to prevent the flow of current between the positive leads of the capacitors and the reference voltage in the discharging state of the switching circuit.

20. The auto darkening eye protection device of claim 19 wherein the directional control circuit includes at least two diodes.

21. The auto darkening eye protection device of claim 18, wherein the negative voltage generator includes:
a switching circuit having a charging state and a discharging-state;
at least two capacitors, the capacitors connected to the switching circuit and a reference voltage to establish charging of the capacitors in the charging state of the switching circuit, and a positive lead of one capacitor electrically connected to a negative lead of another one of the capacitors in the discharging state of the switching circuit;
a directional control circuit connected to the capacitors to permit the flow of current between the negative leads of the capacitors and the reference voltage in the charging state of the switching circuit, and to prevent the flow of current between the negative leads of the capacitors and the reference voltage in the discharging state of the switching circuit.

22. The auto darkening eye protection device of claim 19, wherein the directional control circuit includes at least two diodes.

* * * * *

UNITED STATES PATENT AND TRADEMARK OFFICE
CERTIFICATE OF CORRECTION

PATENT NO. : 6,841,772 B1 Page 1 of 2
APPLICATION NO. : 10/139837
DATED : January 11, 2005
INVENTOR(S) : Thomas J. Hamilton It is certified that error appears in the above-identified patent and that said Letters Patent is hereby corrected as shown below:

The title page, should be deleted to appear as per attached title page.

In the Drawings, FIG. 1, Sheet 1 of 7: Add the reference number to the "Sensor Circuit"

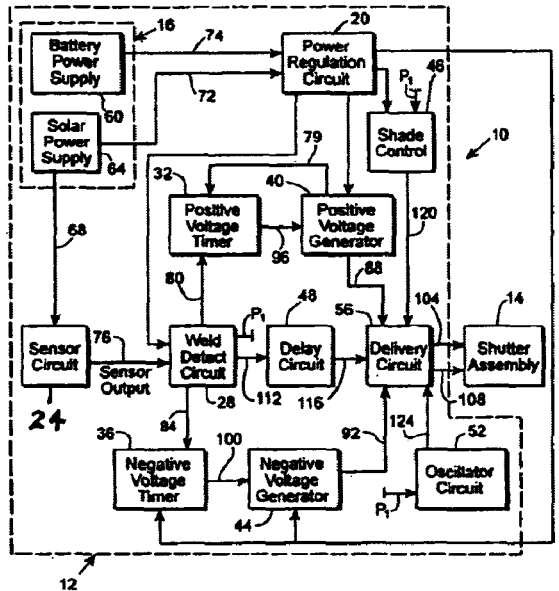

FIG. 1

Signed and Sealed this

Twenty-fourth Day of October, 2006

JON W. DUDAS
*Director of the United States Patent and Trademark Office*

(12) United States Patent
Hamilton

(10) Patent No.: US 6,841,772 B1
(45) Date of Patent: Jan. 11, 2005

(54) EYE-PROTECTION DEVICE HAVING DUAL HIGH VOLTAGE SWITCHING

(75) Inventor: Thomas J. Hamilton, Holland, MI (US)

(73) Assignee: Jackson Products, Inc., St. Charles, MO (US)

(*) Notice: Subject to any disclaimer, the term of this patent is extended or adjusted under 35 U.S.C. 154(b) by 0 days.

(21) Appl. No.: 10/139,837

(22) Filed: May 3, 2002

Related U.S. Application Data

(60) Provisional application No. 60/288,760, filed on May 5, 2001.

(51) Int. Cl.$^7$ ................................................ H01J 40/14
(52) U.S. Cl. .................... 250/214 B; 349/14; 250/201.1
(58) Field of Search ............................ 250/201.1, 250, 250/214 B; 349/13, 14, 116; 359/220

(56) References Cited

U.S. PATENT DOCUMENTS

| | | |
|---|---|---|
| 2,423,320 A | 7/1947 | Hurley |
| 2,548,230 A | 4/1951 | Molyneux |
| 2,761,048 A | 8/1956 | Herrick et al. |
| 3,137,784 A | 6/1964 | Kasemann |
| 3,159,844 A | 12/1964 | Haboush |
| 3,245,315 A | 4/1966 | Marks et al. |
| 3,575,491 A | 4/1971 | Heilmeier |
| 3,731,986 A | 5/1973 | Fergason |
| 3,873,804 A | 3/1975 | Gordon |
| 3,881,808 A | 5/1975 | Gurtler et al. |
| 3,881,809 A | 5/1975 | Fergason et al. |
| 3,890,628 A | 6/1975 | Gurtler |
| 3,918,796 A | 11/1975 | Fergason |
| 3,967,881 A | 7/1976 | Moriyama et al. |
| 4,039,803 A | 8/1977 | Harsch |
| 4,071,912 A | 2/1978 | Budmiger |
| RE29,684 E | 6/1978 | Gordon |
| 4,155,122 A | 5/1979 | Budmiger |
| 4,237,557 A | 12/1980 | Gordon |
| 4,240,709 A | 12/1980 | Hornell |

(List continued on next page.)

FOREIGN PATENT DOCUMENTS

| | | |
|---|---|---|
| DE | DT 2315308 | 10/1973 |
| EP | 0157744 | 9/1985 |
| EP | 0335056 | 4/1989 |
| EP | 0349665 | 10/1990 |
| FR | 2530-039 A | 1/1984 |
| GB | 325586 | 2/1930 |
| JP | 59-92276 | 7/1980 |
| JP | 59-111102 | 6/1984 |
| SE | SW 73127334 | 7/1977 |
| SE | SW 7608690-9 | 2/1979 |
| WO | WO 90/14809 | 12/1990 |

Primary Examiner—Thanh X. Luu
(74) Attorney, Agent, or Firm—Dunlap, Codding & Rogers, P.C.

(57) ABSTRACT

An auto darkening eye protection device comprising a shutter assembly and a control circuit. The shutter assembly is adjustable between a clear state and a dark state. The control circuit comprises a sensing circuit, a weld detect circuit, and a delivery circuit. The sensing circuit senses incident light and provides an output indicative of the incident light. The weld detect circuit receives the output of the sensing circuit, and enables a dark state drive signal to be delivered to the shutter assembly. The delivery circuit outputs the dark state drive signal to the shutter assembly to switch the shutter assembly from the clear state to the dark state upon enablement by the weld detect circuit. The dark state drive signal includes a high voltage pulse followed by a stable AC waveform. The high voltage pulse is formed by a positive voltage signal and a negative voltage signal.

22 Claims, 7 Drawing Sheets